United States Patent [19]

Kraus et al.

[11] Patent Number: 5,552,130
[45] Date of Patent: Sep. 3, 1996

[54] PROCESS FOR THE CONTINUOUS PREPARATION OF NITROSYL CHLORIDE

[75] Inventors: Helmut Kraus, Odenthal; Alexander Klausener, Köln; Heinz Landscheidt, Duisburg, all of Germany

[73] Assignee: Bayer Aktiengesellschaft, Leverkusen, Germany

[21] Appl. No.: 429,277

[22] Filed: Apr. 25, 1995

[30] Foreign Application Priority Data

May 2, 1994 [DE] Germany .......................... 44 15 337.6

[51] Int. Cl.$^6$ ................................................ C01B 21/084
[52] U.S. Cl. ...................... 423/386; 423/462; 546/345; 548/373.1
[58] Field of Search ........................... 423/386, 659

[56] References Cited

U.S. PATENT DOCUMENTS

| | | |
|---|---|---|
| 2,366,518 | 1/1945 | Grebe et al. . |
| 3,214,240 | 10/1965 | Beekhuis . |
| 3,290,115 | 12/1966 | Smal et al. ................ 423/386 |
| 3,481,704 | 12/1969 | Van Der Plas ........................ 423/386 |
| 3,660,030 | 5/1972 | Colebourne et al. .................... 423/386 |
| 4,026,674 | 5/1977 | McDonald .............................. 423/659 |
| 4,557,920 | 12/1985 | Rissmann et al. . |
| 4,996,035 | 2/1991 | Stepaniuk et al. ....................... 423/386 |
| 5,283,338 | 2/1994 | Cramm et al. . |

FOREIGN PATENT DOCUMENTS

| | | |
|---|---|---|
| 0508215 | 10/1992 | European Pat. Off. . |
| 1333767 | 6/1963 | France . |
| 1169903 | 5/1964 | Germany . |
| 2019216 | 10/1970 | Germany . |
| 786740 | 11/1957 | United Kingdom . |
| 1280223 | 4/1972 | United Kingdom . |
| 9009958 | 9/1990 | WIPO . |

OTHER PUBLICATIONS

M. Tuot et al. Comptes Rend, vol. 204, pp. 697–684 (1932).
J. Wise et al., J. Chem. Phys, vol. 18, p. 1411 (1950).
L. Harris et al., J. Am. Chem. Soc., vol. 63, pp. 2520–2523 (1942).
Abstract of F.R. 1,333,767 (1962).

*Primary Examiner*—Wayne Langel
*Attorney, Agent, or Firm*—Sprung Horn Kramer & Woods

[57] ABSTRACT

The reaction of nitrogen dioxide with hydrogen chloride to give nitrosyl chloride and nitric acid can be advantageously carried out in cocurrent in a reactor in such a way that the reactants are introduced at the bottom and the nitrosyl chloride is taken off at the top and the nitric acid is taken off at the bottom of the reactor.

5 Claims, No Drawings

PROCESS FOR THE CONTINUOUS PREPARATION OF NITROSYL CHLORIDE

The invention relates to a continuous process for preparing chlorine-free nitrosyl chloride from gaseous nitrogen dioxide and gaseous hydrogen chloride. For the purposes of the present invention, the term "nitrogen dioxide" includes the dinitrogen tetroxide in equilibrium therewith.

Nitrosyl chloride is a NO⊕ source frequently used in organic chemistry, for example for oximations, nitrosations and diazotizations. Numerous processes have been described for preparing nitrosyl chloride.

The best known preparative method for nitrosyl chloride is the preparation of aqua regia, which however also forms chlorine:

$$3\ HCl + HNO_3 \rightarrow NOCl + Cl_2 + H_2O$$

Passing hydrogen chloride into a solution of nitrosylsulphuric acid in sulphuric acid leads to the formation of nitrosyl chloride according to the equation.

$$NOHSO_4 + HCl \rightarrow NOCl + H_2SO_4$$

In this method, the conversion is continuously reduced as the reaction progresses, so that nitrosyl chloride/hydrogen chloride mixtures having a continually falling proportion of nitrosyl chloride are formed. The disposal of the sulphuric acid containing chloride and nitrogen oxides, which is formed as a byproduct, is technically complicated.

Some other processes start out from nitrogen monoxide: according to German Auslegeschrift 1 169 903 recommends the reaction with chlorine in the presence of a catalyst in accordance with the equation $$2\ NO + Cl_2 \xrightarrow{cat.} 2\ NOCl$$

According to U.S. Pat. No. 2,366,518, the reaction with gaseous hydrogen chloride in the presence of oxygen proceeds via dinitrogen trioxide:

$$2\ NO + \tfrac{1}{2}O_2 \rightarrow N_2O_3$$

$$N_2O_3 + 2HCl \rightarrow 2NOCl + H_2O.$$

According to Comptes Rend. 204 (1932), 697 to 699, anhydrous nitrosyl chloride is obtained by reaction of dinitrogen trioxide with thionyl chloride:

$$N_2O_3 + SOCl_2 \rightarrow 2NOCl + SO_2$$

The said processes have the disadvantage that they require nitrogen monoxide, which is not readily available in the industry, as starting material.

The formation of nitrosyl chloride from alkyl nitrites in a low-salt medium is utilized, for example, in diazotization:

$$RONO + HCl \rightleftharpoons NOCl + ROH$$

$$C_6H_5-NH_2 + NOCl \rightarrow C_6H_5-N_2^{\oplus}Cl^{\ominus}$$

However, the alcohol also formed can lead to undesired byproducts via a Sandmeyer reaction. Furthermore, alkyl nitrites are usually prepared from sodium nitrite, sulphuric acid and alcohol; owing to the high amount of salt formed, this method is thus not particularly well suited to a preparation on an industrial scale.

Other processes for preparing nitrosyl chloride start out from nitrogen dioxide which is readily available in the industry. According to British Patent Specification 786 740 and French Patent Specification 1 333 767, nitrogen dioxide is passed into moistened alkali metal or alkaline earth metal chloride, but large amounts of alkali metal or alkaline earth metal nitrate are obtained as byproduct. According to J. Chem. Phys. 18 (1950), 1411, this gives a mixture of nitrosyl chloride, nitroxyl chloride and nitrogen dioxide.

In the reaction of nitrogen dioxide with gaseous hydrogen chloride, according to J. Amer. Chem. Soc. 63 (1942), 2520 chlorine is formed as byproduct according to the equation:

$$NO_2 + 2\ HCl \rightarrow NOCl + H_2O + \tfrac{1}{2}Cl_2$$

According to U.S. Pat. No. 2,366,518, this gives only a small amount of nitrosyl chloride became of byproduct formation (nitroxyl chloride, nitric acid, nitrogen oxides).

According to German Offenlegungsschrift 2 019 216, nitrosyl chloride is prepared by reaction of liquid nitrogen dioxide and gaseous hydrogen chloride in nitric acid and subsequently has to be isolated batchwise.

The object of the invention is to provide a process which can be operated continuously and starts out from nitrogen dioxide, which is readily available in the industry, for preparing nitrosyl chloride in good yield and in a purity which allows the nitrosyl chloride formed to be used without further purification steps for the chlorination via diazotization of aminoheterocycles, e.g. aminopyridines and aminopyrazoles, while avoiding byproducts which are difficult to separate off and difficult to dispose of, such as chlorine, nitrogen oxides and, in particular, large amounts of salt. The nitric acid formed here should be of sufficient quality to enable its further use without additional purification measures.

It has now surprisingly been found that with a suitable arrangement nitrogen dioxide and hydrogen chloride can be reacted almost quantitatively in the gas phase to give nitrosyl chloride of high purity.

The invention accordingly provides a process for preparing nitrosyl chloride from hydrogen chloride and nitrogen dioxide in a molar ratio of from 0.4 to 1, preferably from 0.4 to 0.8, in particular from 0.5 to 0.7, at temperatures of from 0° to 100° C., preferably from 0° to 60° C., according to which the reactants are passed through a reactor in cocurrent from the bottom upwards and the nitrosyl chloride formed is taken off at the top and the nitric acid formed is taken off at the bottom of the reactor.

The reactants can be used as such or in a mixture with inert gases. Such inert gases include, for example, nitrogen, carbon dioxide, argon and the other noble gases. Such an inert gas can be fed into the reactor separately or premixed with one or both reactants. The volume ratio inert gas/nitrogen dioxide can be, for example, from 0 to 15, preferably from 0.1 to 8. The co-use of water is not necessary in the process of the invention; however, small amounts can be advantageous for diluting the nitric acid formed.

Excess hydrogen chloride can, after condensation of the nitrosyl chloride, optionally together with the inert gas, be removed and recycled to the reaction.

The process of the invention can in principle be carried out either at atmospheric pressure or at reduced or elevated pressure. The suitable pressure range is from 0.5 to 10 bar, preferably from 0.7 to 7 bar, particularly preferably from 1 to 5 bar.

Reactors to be used for the process of the invention and the reaction conditions are selected in such a way that sufficient residence time for complete conversion is ensured.

Suitable reactors include, for example, reaction columns which ensure a large phase interface (gaseous/liquid) and intimate mixing of the liquid and gaseous phases. This can be achieved by the installation of trays, such as bubble trays, perforated trays, valve trays, slot trays, etc., as are customary for a thermal separation, by column packings of all types, as are customary in thermal separation operations, or by equipping the columns with random column packings of all types or with ordered packings of metal, ceramic, plastic, glass or further materials which are inert to the reactants of the process of the invention. Such columns with internal fittings or packings and the packings themselves are commercially available and known to those skilled in the art.

Preferred reactors are of tubular construction and possess a length/diameter ratio of from 10 to 150, preferably from 20 to 70. Particularly preferred reactors are packed columns as are used for fractional distillation in a non-horizontal, i.e. in vertical or even oblique, arrangement.

The optimum size of the phase interface required in the reactor also depends on temperature and amount of gas. However, surface area/volume ratios of from 1 to 20 $cm^{-1}$, preferably from 5 to 15 $cm^{-1}$, generally give satisfactory results. The throughput of the reactors, based on the total amount of gas fed in (nitrogen dioxide, hydrogen chloride and optionally inert gas), is generally from 10 to 3000, preferably from 20 to 2000 and particularly preferably from 40 to 1000, standard l/l of free volume in the reaction column per hour (standard l=litres at STP).

The invention further provides for the use of the nitrosyl chloride prepared according to the invention in chlorinations via diazotization of aminoheterocycles such as aminopyridines and aminopyrazoles.

The gas ratios of the following examples are by volume; percentages are by weight.

EXAMPLES

Apparatus used:

A glass column having a length of 80 cm and an internal diameter of 2 cm was packed with glass spheres having a diameter of 3 mm. The reactants were introduced at the bottom end. The top of the column was cooled using dry ice; the condensed nitrosyl chloride was taken off there.

Example 1

15 l/h of a hydrogen chloride/nitrogen mixture (15:85) and, after 10 minutes, 1 l/h of nitrogen dioxide having a temperature of 25° C. were passed in at the bottom end of the column maintained at 25° C.

25 ml of DMF were sainted with hydrogen chloride in a 500 ml flask. After dilution with 200 ml of DMF and Cooling to −10° C., 20 ml of the crude NOCl prepared were added. At 0° C., a solution of 17.3 g of 2-amino-5-aminomethylpyridine in 100 ml of DMF was added dropwise. After warming to room temperature and stirring for a further 1 hour, the mixture was evaporated on a rotary evaporator. The crude product was neutralized with 0.2N sodium hydroxide solution and extracted with dichloromethane. After drying with anhydrous sodium sulphate and evaporation on a rotary evaporator, there were obtained 14.2 g of product which, according to GC with internal standard, contained 85.8% of 2-chloro-5-chloromethylpyridine (61.4% of theory).

Example 2

Through the glass column, 20 l/h of a hydrogen chloride/nitrogen mixture (15:85) were passed for 1 hour into a solution of 2.6 g of 94.5% strength 2-amino-5-aminomethylpyridine in 70 ml of DMF. After cooling the mixture to 0° C., 2 l/h of nitrogen dioxide were additionally fed into the column for 1 hour. After customary workup, 2-chloro-5-chloromethylpyridine was obtained in a yield of 72.4% of theory. 2.2% of 2-chloro-5-hydroxymethylpyridine and 0.4% of 2,6-dichloro-5-chloromethylpyridine were identified as byproducts. The aqueous phase contained about 20% of theory of 5-chloromethylpyrid-2-one, which can in a known manner be likewise converted into 2-chloro-5-chloromethylpyridine.

Example 3

Through the glass column, 8 l/h of a hydrogen chloride/nitrogen mixture (15:85) were passed for 1 hour into a solution maintained at 0° C. of 8.5 g of ethyl 1-methyl-5-aminopyrazolecarboxylate in 100 ml of chloroform. 8 l/h of nitrogen dioxide were then added for 1 hour. The reaction mixture was evaporated in vacuo, dissolved in 100 ml of concentrated hydrochloric acid and a solution of 31 g of copper sulphate and 28 g of sodium chloride in 100 ml of water was subsequently added dropwise. After stirring for 1.5 hours at 50° C., the mixture was extracted with chloroform, the combined extracts were dried using anhydrous sodium sulphate and evaporated on a rotary evaporator. Ethyl 1-methyl-5-chloropyrazole-4-carboxylate was obtained in a yield of 76.7% of theory.

We claim:

1. A gas phase process for preparing pure nitrosyl chloride which consists essentially of continuously introducing hydrogen chloride and 0.4 to 1 times its molar amount of nitrogen dioxide at the bottom of a reactor, continuously taking off nitrosyl chloride from the top of the reactor, and continuously taking off nitric acid at the bottom of the reactor, the reaction being effected in the presence of little or no water.

2. The process according to claim 1, wherein the nitrogen dioxide is introduced in 0.4 to 0.8 times the molar amount of the hydrogen chloride.

3. The process according to claim 1, wherein the nitrogen dioxide is introduced in 0.5 to 0.7 times the molar amount of the hydrogen chloride.

4. The process according to claim 1, wherein the reaction mass is substantially free of water.

5. The process according to claim 4, wherein the nitrogen dioxide is introduced in 0.5 to 0.7 times the molar amount of the hydrogen chloride, and the hydrogen chloride and nitrogen dioxide are introduced in gaseous state.

* * * * *